US006429299B1

(12) United States Patent
Bowler et al.

(10) Patent No.: US 6,429,299 B1
(45) Date of Patent: Aug. 6, 2002

(54) NUCLEOTIDE SEQUENCES ENCODING THE TOMATO LIGHT HYPERSENSITIVE PHENOTYPE, ENCODED PROTEINS AND USES THEREOF

(75) Inventors: Chris Bowler; Anna Chiara Mustilli, both of Naples (IT)

(73) Assignee: Stazione Zoologica "Anton Dohrn", Naples (IT)

( * ) Notice: Subject to any disclaimer, the term of this patent is extended or adjusted under 35 U.S.C. 154(b) by 0 days.

(21) Appl. No.: 09/555,889
(22) PCT Filed: Dec. 7, 1998
(86) PCT No.: PCT/IT98/00350
  § 371 (c)(1),
  (2), (4) Date: Aug. 3, 2000
(87) PCT Pub. No.: WO99/29866
  PCT Pub. Date: Jun. 17, 1999

(30) Foreign Application Priority Data

Dec. 9, 1997 (IT) ........................................ RM97A0760

(51) Int. Cl.[7] ........................ C07H 21/02; C07H 21/04; C12Q 1/68
(52) U.S. Cl. .................... 536/23.1; 536/22.1; 536/24.3; 536/24.5; 435/6; 435/91.2; 435/320.1; 800/290
(58) Field of Search .............................. 536/23.1, 24.3, 536/24.5, 22.1; 435/6, 91.2, 320.1; 800/290

(56) References Cited

FOREIGN PATENT DOCUMENTS

| WO | WO 96/13149 | 5/1996 |
|----|-------------|--------|
| WO | WO 97/14807 | 4/1997 |
| WO | WO 97/20941 | 6/1997 |
| WO | WO 97/39112 | 10/1997 |

OTHER PUBLICATIONS

Boylan, M. T., et al (1989). "Oat Phytochrome is Biologically Active in Transgenic Tomatoes," *The Plant Cell* 1:765–773.

Fray, R.G., et al. (1995). "Constitutive expression of a fruit phytoene synthase gene in transgenic tomatoes causes dwarfism by redirecting metabolites from the gibberellin pathway," *The Plant Journal* 8:693–701.

Ganal, M.W., et al. (1998) "CT151.KS Tomato leaf cDNA from cv. VFNT cherry *Lycopersicon esculentum* cDNA clone CT151." EMBL Accession No. AA824865. (Total of 1 page).

Kerckhoffs, L.H.J., et al. (1997). "Photocontrol of Anthocyanin Biosynthesis in Tomato," *J. Plant Res.* 110:141–149.

Kerckhoffs, L.H.J., et al. (1997). "Physiological Characterization of Exaggerated–Photoresponse Mutants of Tomato." *J. Plant Physiol.* 150:578–587.

McNellis, T.W., et al. (1996). "Expression of an N–Terminal Fragment of COP1 Confers a Dominant–Negative Effect on Light–Regulated Seeding Development in Arabidopsis." *The Plant Cell* 8:1491–1503.

McNellis, T.W., et al. (1994). "Overexpression of Arabidopsis COP1 Results in Partial Suppression of Light–Mediated Development : Evidence for a Light–Inactivable Repressor of Photomorphogenesis." *The Plant Cell* 6:1391–1400.

Mustilli, A.C., et al. (1999). "Phenotype of the Tomato high pigment–2 Mutant is Caused by a Mutation in the Tomato Monolog of Deetiolated1." *The Plant Cell* 11:145–157.

Pepper, A., et al. (1994). "DET1, a Negative Regulator of Light–Mediated Development and Gene Expression in Arabidopsis, Encodes a Novel Nuclear–Localized Protein." *Cell* 78:109–116.

Tanksley, S.D., et al. (1992). "High Density Molecular Linkage Maps of the Tomato and Potato Genomes." *Genetics* 132:1141–1160.

vanTuinen, A., et al. (1997). "The mapping of phytochrome genes and phtomorphorenic mutants of tomato." *Theor. Appl. Genet.* 94:115–122.

Yen, H.C., et al. (1997) "The tomato high–pigment (hp) locus maps to chromosome 2 and influences plastome copy number and fruit quality." *Theor. Appl. Genet.* 95:1069–1079.

*Primary Examiner*—Jeffrey Fredman
(74) *Attorney, Agent, or Firm*—Rothwell, Figg, Ernst & Manbeck

(57) ABSTRACT

Nucleotide sequences of the tomato TDET1 (HP-2) gene are described, which sequences, if modified, result in a light hypersensitive phenotype. Vectors and uses for the production of transgenic plants are also described and transgenic plants so obtained.

27 Claims, 10 Drawing Sheets

Figure 1:
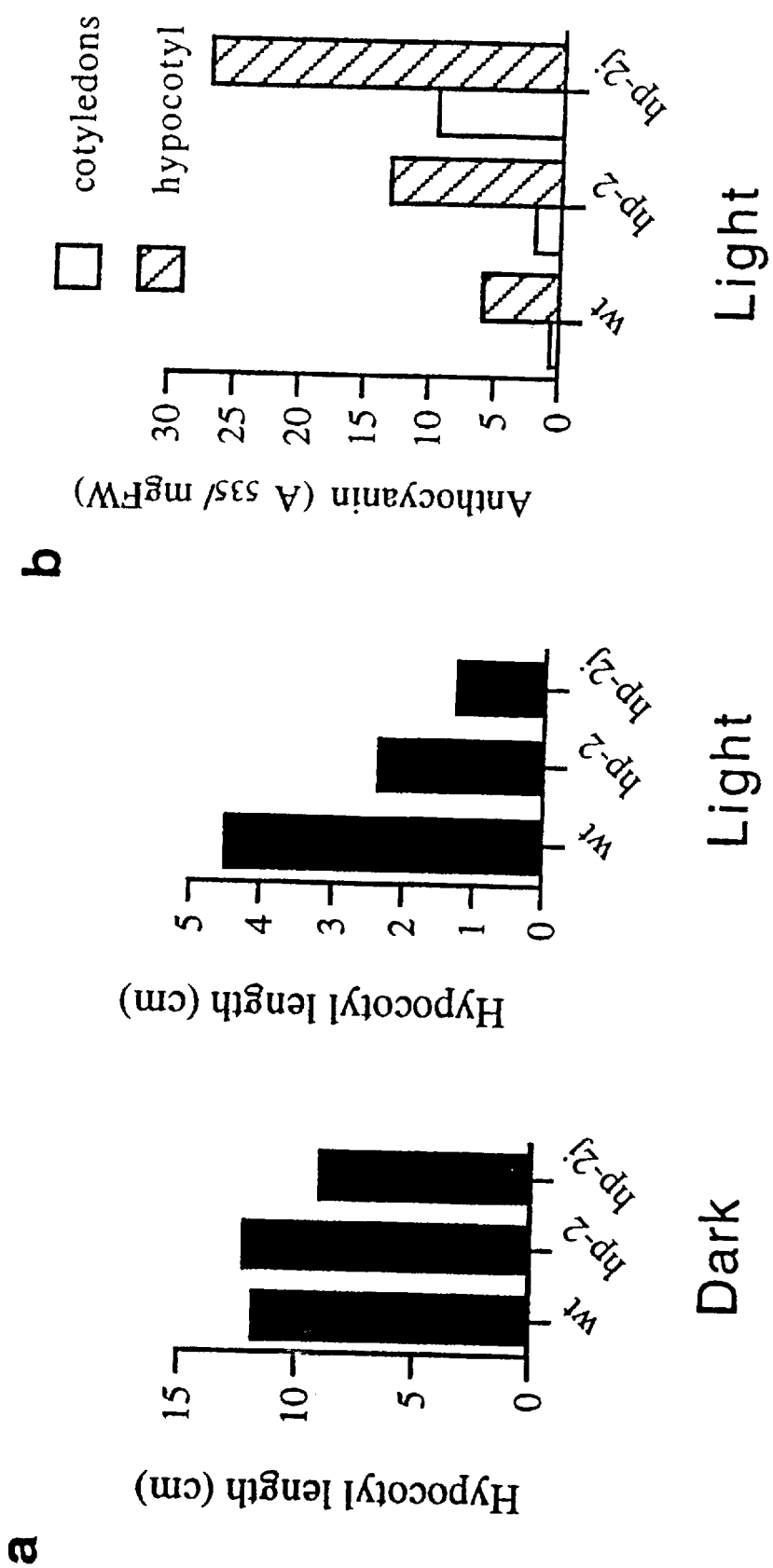

```
   1  cttccctctt agactttatc gatcctaatt cgagccctcc ttttttcaat
  51  caattatcaa tttagtccta ctgcgatttt gatatgtatg attcacaatt
 101  ttaatgctgc tgaaagcaat tatataaaag ctgaaacatt ttgcactgAT
 151  GTTCAAAACT AACAATGTTA CCGCCAGGCT TTTTGAGCGC CAGATTTGCA
 201  CCCCTGCTCC TGGCACCAGC ATCCATCGTG CCAGAAGATT TTATGAGAAC
 251  GTTGTACCAA GTTATACCAT ATACGATGTT GAATGTCCCG ACCATTCATT
 301  TCGCAAGTTC ACGGATGACG GTCTATATTT TGTAAGTTTC AGCCGAAACC
 351  ATCAGGATCT GGTTGTTTAT AGACCAACAT GGCTGACATT TTCCTGCAAA
 401  GAAGAAGATT GTGATACTCA TGATCTTCCT TTGAAAGCTA GAAAGTTTGA
 451  GAGCTTCTTC ACACAGTTGT ACAGTGTTAC TCTTGCTTCT AGTGGGGAAC
 501  TTATATGCAA AGATTTCTTT CTCTATATGG AGAGCAACCA ATTTGGACTC
 551  TTTGCAACTT CAACTGCACA AATTCATGAT GCACCTCCTA CTGGAGGGGC
 601  AATTCAGGGA GTCCCTTCAG TTGAAAAAAT AACTTTCCAC CTTTTGAGGT
 651  TGGTGGATGG AGCTATACTT GACGAAAGGG TTTTCCACAA TGATTATGTT
 701  AATTTGGCAC ATAGCATTGG TGCTTTCTTG TATGATGATT TGCTTGCTAT
 751  AGTGTCTCTT CGTTATCAAA GAATACACAT CCTTCAGATC AGAGATTCTG
 801  GAGATCTTGT TGATGTACGA GCAATTGGGG AATTCTGCCG TGAAGATGAT
 851  GAACTTTTTC TCAATTCCAA TTCCCAGGTG CTTGTAAATC ATGTTGGAAA
 901  TGGTTTTCAT CATAGTCTGC CTCAATCAGA AACTTCTTTC CTGAGCGGTA
 951  TAAAGCAACG GCTGCTTTCA TATATATTTC GAGGTATATG GAATGAAGCT
1001  GACCAAACCA TGAGAGTGCA GTGCCTGAAG AAGAAGTTTT ACTTCCACTT
1051  TCAAGATTAC ATTGACTTGA TTATCTGGAA GGTGCAGTTT TTGGACCGAC
1101  ATCACCTGTT GATCAAGTTT GGCAGTGTTG ATGGTGGGGT ATCCCGAAAT
1151  GCTGACATCC ATCCTTCTTT TTTTGCTGTT TACAATATGG AGACTACTGA
1201  AATTGTTGCA TTTTATCAGA ACTCAGCCGA TGAGCTTTAT TTCTTGTTCG
1251  AGCTGTTCAG CGACCATTTT CACGTTTCAT CCAAAAGTTC ATTACATATG
1301  AACTTCATGT CCTCACACTC AAACAACATC CACGCCCTCG AGCAACTAAG
1351  GTGTACAAAG AACAAAGCAA CCAATTTCTC TCAATTTGTT AAGAAAATGA
1401  TGGCTTCCTT GCCTTGTAGT TGTCAGTCTC AGAGTCCTTC CCCATATTTT
1451  GACCAATCTC TCTTCAGGTT TGACGAGAAG CTTATTTCAG CTATTGACCG
1501  CCATAGACAG TCTACTGACC ATCCAATCAA ATTCATTTCT AGAAGACAAC
1551  CCAATATCCT GAAATTCAAA ATGAAGCCAG GACCTGAAGC TGGCAGCACA
1601  GATGGGCGAA CTAAGAAGAT CTGTTCCTTC CTCTTCCACC CAATATTACC
1651  CCTTGCACTT TCTGTTCAAC AAACCTTGTT TCTGCAGGCA TCAGTTGTAA
1701  ATATCCATTT TCGTCGATAA tgtaaaaact taatttatat gttaccgatt
1751  tgtttataaa tttctctaat aacctctaga ttgaaatcaa cctagaaatc
```

Fig. 2

```
1801  acaaattcat cataacagac ccgtagatgc tagtgtctttt gacttctaca
1851  ttttctttgt tacaagaatc aaacaaatgc ttgatagagt gccaagacgg
1901  ttagtatggg tataaggatt agttcttctg taagttttg ttacagcttc
1951  tcttctaatt aattgatgta cattcagatg tttaaaaaaa aaaaaaaaaa
```

Fig. 2'

```
  1  MFKTNNVTAR  LFERQICTPA  PGTSIHRARR  FYENVVPSYT  IYDVECPDHS
 51  FRKFTDDGLY  FVSFSRNHQD  LVVYRPTWLT  FSCKEEDCDT  HDLPLKARKF
101  ESFFTQLYSV  TLASSGELIC  KDFFLYMESN  QFGLFATSTA  QIHDAPPTGG
151  AIQGVPSVEK  ITFHLLRLVD  GAILDERVFH  NDYVNLAHSI  GAFLYDDLLA
201  IVSLRYQRIH  ILQIRDSGDL  VDVRAIGEFC  REDDELFLNS  NSQVLVNHVG
251  NGFHHSLPQS  ETSFLSGIKQ  RLLSYIFRGI  WNEADQTMRV  QCLKKKFYFH
301  FQDYIDLIIW  KVQFLDRHHL  LIKFGSVDGG  VSRNADIHPS  FFAVYNMETT
351  EIVAFYQNSA  DELYFLFELF  SDHFHVSSKS  SLHMNFMSSH  SNNIHALEQL
401  RCTKNKATNF  SQFVKKMMAS  LPCSCQSQSP  SPYFDQSLFR  FDEKLISAID
451  RHRQSTDHPI  KFISRRQPNI  LKFKMKPGPE  AGSTDGRTKK  ICSFLFHPIL
501  PLALSVQQTL  FLQASVVNIH  FRR
```

Fig. 3

```
S. lycopersicum:   1 M----------FKTNNVTARLFERQICTPAPGTSIHRARRFYENVVPSYTIYDVECPDH
   A. thaliana:   1 M----------FTSGNVTARVFERQIRTPPGASVNRARHFYENLVPSYTLYDVESPDH
  Mammals EST:    1 MDHHVSTIKPRRIQNQNVIHRLERRRISSGKAGTHWHQVRVFHQNVFHNFTVVNVEKHPC 50 SFRKFTDDGLYFVSFSRNHQDLVVYRPTWLTFSCKEEDCDTL-HDLPLKARKFESFFTQLY
                  50 CFRKFTEDGLFLISFSRNHQELIVYRPSWLTYSTTDDSTTTLPPLPRRASKFDSFFTQLY
                  61 FLRKFSPDGRYFIAFSSDQTSLEIM------------------------EYQG-----

109 SVTLASSGELICKDFFLYMESNQFGLFATSTAQIHDAP-PTGGAIQGVPSVEKITFHLLR
                 110 SVNLASSNELICKDFFLYHQTRRFGLFATSTAQIHDSSSPSNDAVPGVPSIDKITFVLLR
                  90 ------------QQA-------------------------------------

168 LVDGAILDERVFHNDYVNLAHSIGAFLYDDLLAIVSLRYQRIHILQIRDSGDLVDVRAIG
                 170 LDDGVVLDERVFLHDFVNLAHNMGVFLYDDLLAILSLRYQRIHLLQIRDSGHLVDARAIG
                  93 -------AEDRTFKCDKMVLSHNQGLYLYKNILAILSVQQDTIHVFCVTPEGTFIDVRTIG

228 EFCREDDELFLNSNSQVLVNH----------------VGNGFHHSLPCSETS--FLSGIK
                 230 YFCREDDELFLNSSSQAMMSQDKSKQCSLSGSKEDDTGENGLRHSLSQFSGSNSFLSGVK
                 147 RFCYEDQLLTVS----AVFPEVKRDSQT----------GMANPFRDH----FINSLK

270 QRLLSYIFRGIWNEADQTMRVQCLKKKFYFHFQDYIDLIIWKVQFLDRHHLLIKFGSVDG
                 290 QRLLSFIFREIWNEESDN-RVQSLKKKFYFHFQDYVDLIIWKVQFLDRQHLLIKFGSVDG
                 186 HRLLVML----MRRAEGDGSAMA-KRRFFQYHDQTAALRMWKMQLLDENHLFIKYTSEDV

330 GVSRNADI-HPSFFAVYNMETTEIVAFYQNSADELYFLFELFSDHFHVSSKSSLHMNFMS
                 349 GVTRSADH-HPAFFAVYNMETTDIVAFYQNSAEDLYQLFEQFSDHFTVSSSTPF-MNFVT
                 241 VTLRVTDPSQASFFVVYNMVTTEVIAVFENTSDELLELFENFCDLFR-NATLHSEVCFPC

389 SHSNNIHALEQLRCTKN----KATNFSQFVKKMMASLPCSCQSQSPSPYFDQSLFRFDE
                 407 SHSNNVYALEQLKYTKN----KSNSFSQFVKKMLLLSLRFSCQSQSPSPYFDQSLFRFDE
                 300 SASSNNFARQIQRRFKDTIINAKYGGHTEAMRRLLGQLFISAQSYSGSPYLQLSLFSYDD
                                                              * * *              +

444 KLISAIDRHRQSTDHPIKFISRRQPNILKFKMKPGPEAGSTDGRTKKICSFLFHPILPLA
                 462 KLISAADRHRQSSDNPIKFISRRQPQTLKFKIKPGPECGTADGRSKKICSFLFHPHLPLA
                 360 KWWSVMERPKTCGDHPIRFYAH-DSGLLKFELQAGLLGRPINHTVRRLVAFF--------

504 LSVQQTLFLQASVVNIHFRR
                 522 ISIQQTLFMPPSVVNIHFRR
                 410 -----------------T
```

Fig. 5

NUCLEOTIDE SEQUENCES ENCODING THE TOMATO LIGHT HYPERSENSITIVE PHENOTYPE, ENCODED PROTEINS AND USES THEREOF

The present invention relates to nucleotide sequences encoding the tomato light hypersensitive phenotype, encoded proteins and uses thereof.

In particular the present invention relates to nucleotide sequences encoding a protein, whose qualitative or quantitative modification and/or inhibition in plants induces high levels of carotenoids and/or flavonoids and/or chlorophylls, in comparison with wild-type plants; the invention also relates to the use of these nucleotide sequences for the production of engineered plants to be employed in the agro-industrial sector.

Light is a critical environmental signal that controls many aspects of plant growth and development. It is perceived by a sophisticated series of photoreceptors: the phytochromes, which absorb red and far red light, the cryptochromes, which absorb blue and UV-A light wavelengths, and the UV-B receptors (Mustilli and Bowler, 1997). Together with endogenous hormonal signals, these photoreceptors regulate the developmental changes known as photomorphogenesis. Photomorphogenesis is defined as the influence of light on plant development and comprises leaf and chloroplast development and the regulation of photosynthetic apparatus components, by means of the coordinated expression of both nuclear and cytoplasmic genes. Moreover, due to the light response, photoprotectant pigments such as flavonoids are also produced. The modifications occurring during photomorphogenesis have been characterized by studying light effects on Arabidopsis seedling development (von Arnim and Deng, 1996). Light-grown Arabidopsis seedlings display short hypocotyls, open and expanded cotyledons and the expression of light-regulated genes which are responsible for flavonoid and chlorophyll biosynthesis (e.g. chalcone synthase, CHS; chlorophyll A/B binding protein, CAB). Dark-grown seedlings display elongated hypocotyls, closed cotyledons and repression of light-regulated genes.

In higher plants, the phytochromes are encoded by a gene family (e.g. PHYA-E in Arabidopsis, Sharrock and Quail, 1989; Clack et al., 1994) and although they are the best characterized photoreceptors, relatively little is known about how the light signals perceived by phytochromes are transduced to the nucleus to activate the various developmental, physiological and molecular responses to light. Recently, biochemical studies using microinjection into cells of the phytochrome deficient aurea (au) tomato mutant, along with pharmacological studies in photomixotrophic soybean cell cultures, have implicated heterotrimeric G-proteins, cGMP, calcium and calmodulin as intermediates in phytochrome signal transduction pathways (Bowler and Chua, 1994; Mustilli and Bowler, 1997). In parallel, several genetic screens have been developed to identify mutants potentially affected in light signal transduction (Chamowitz and Deng, 1996). Most of the photomorphogenic mutants have been characterised in Arabidopsis and can be classified as either insensitive or constitutive mutants. Insensitive mutants display a light-blind elongated phenotype in the light. Some are mutated in the photoreceptors themselves, whilst others are presumed to encode positive regulators of light signal transduction pathways (Chamovitz and Deng, 1996; Chory et al., 1996; Whitelam and Harberd, 1994). Conversely, constitutive de-etiolated mutants (e.g. cop/det/fus/cpd) display light grown morphologies when grown in the dark together, in some cases, with the inappropriate expression of light regulated genes such as CAB and CHS (Millar et al., 1994; Szekeres et al., 1996). The recessive nature of these mutations suggests that they are loss-of-function and that the wild-type genes are repressors of photomorphogenesis in darkness. However, although epistasis tests with phytochrome-deficient mutants have indicated that they function downstream of phytochrome, they are not specifically mutated in phytochrome signal transduction because many have altered tissue specificities as well as other additional phenotypes not directly related to light (Mayer et al., 1996; Chory and Peto, 1990; Millar et al., 1994; Szekeres et al., 1996). It is therefore not clear how COP/DET/FUS/CPD proteins function in the signal transduction pathways defined biochemically (Bowler and Chua, 1994).

A more targeted approach to identify specific components of signal transduction pathways specific for phytochrome could be the isolation of mutants with altered dynamics of light responses, rather than mutants with constitutive phenotypes in the absence of light. Several such light hypersensitve mutants have already been isolated in tomato (denoted hp-1, hp-2, atv, Ip; Kendrick et al., 1994). In particular, the recessive non-allelic hp-1 and hp-2 mutants have been characterized by their exaggerated light responsiveness, displaying higher anthocyanin levels (a flavonoid subgroup), shorter hypocotyls and more deeply pigmented fruits than wild-type plants. These mutants were first identified in 1917 (Reynard, 1956) and in 1975 (Soressi, 1975), respectively. Recently, hp-1$^w$ (Peters et al., 1989) and hp-2$^j$ (Van Tuinen et al., 1997) mutants have been isolated and identified as new hp-1 and hp-2 alleles, respectively. Because these phenotypes appear to be identical to those obtained by ectopic expression of phytochrome A (PHYA) in tomato (Boylan and Quail, 1989), it would appear that the hp mutation may affect fairly specifically phytochrome responses. The recessive nature of the mutations, coupled with results from epistasis tests of hp-1 with the phytochrome deficient tomato mutants aurea (au), phyA (fri), and phyB (tri), have suggested that HP genes encode negative regulators of light signal transduction mechanisms, acting downstream of both PhyA and PhyB (Kerckhoffs et al., 1997). The fact that no counterparts of hp mutants have been isolated so far in Arabidopsis, along with the observation that in tomato anthocyanin production and the expression of photoregulated genes (e.g., CHS and CAB) is strictly light-dependent, indicates the importance of hp mutants for studying phytochrome-dependent signal transduction. Furthermore, microinjection-based studies using the au tomato mutant have shown that tomato is an excellent model system to map the role of individual components in the phytochrome activated signalling cascade (Bowler and Chua, 1994). Therefore the identification and characterization of hp genes is likely to be very important for studying the regulation of photomorphogenesis in plants.

The authors of the present invention have cloned the tomato HP-2 gene and have studied at the molecular level the role of the HP-2 protein during the modulation of photomorphogenesis and fruit development. The authors have found that the tomato HP-2 gene exhibits high sequence homology with the Arabidopsis DET1 gene, which belongs to the above described constitutive COP/DET/FUS mutant group. Therefore the tomato HP-2 gene has been renamed TDET1.

The authors have used Solanum lycopersicum (tomato) species plants, but those skilled in the art will recognize that the cloning could be repeated with no inventive efforts with other plant species, as but not limited to pepper, eggplant, soybean, grape, melon, rice, carrot, spinach, citrus, pomaceae and ornamental species. The authors have cloned and sequenced the gene responsible for the tomato hp mutation (high pigment), which causes a light hypersensitive phenotype, thus enhancing carotenoid, and/or chlorophyll and/or flavonoid pigment levels. The gene is the first to be identified that causes such a mutant phenotype.

hp mutants potentially have a direct application in the agro-industrial sector, for generating tomato fruits with high carotenoid and/or flavonoid contents. In particular, in tomato fruits of hp mutants, a high content of the carotenoid lycopene as well as other carotenoids and flavonoids has been observed(Thompson, 1955; Yen et al., 1997). However, up to now the use of hp mutants in the agro-industrial sector, even if bred into various commercial varieties, has been impaired because of the fact that the hp mutation generates other undesirable phenotypes, such as reduced internode length and reduced plant vigour.

The cloning of the TDET1 gene and its use by means of gene transfer technologies offers considerable advantages with respect to conventional breeding techniques. It is possible to transfer genes suitable for agriculture between different species and to inactivate and/or engineer genes of the same species, even only in specific plant tissues. Furthermore gene transfer is a much more rapid technique than conventional breeding.

The cloning of the TDET1 gene now allows the production of engineered plants which exhibit all the favourable features of the hp mutation, with none of the undesirable side-effects. Such plants could belong to the Solanum genus, but those skilled in the art will recognize that, with no inventive effort, it is possible to transfer the gene, or parts thereof, subcloned in suitable expression vectors, into plants belonging to different genera, as e.g. but not limited to pepper, eggplant, soybean, grape, melon, rice, carrot, spinach, citrus, pomaceae and ornamental species.

It has been well recognized that a diet rich in lycopene and other carotenoids, or their administration in the form of pills, produce favourable effects on human health. As a matter of fact, carotenoids have antioxidant properties, β-carotene is a pro-vitamin A and lycopene is known to be an effective antitumoral agent (Bartley and Scolnik, 1995; Giles and Ireland, 1997; Hoffmann and Weisburger, 1997; Pappalardo et al., 1997; Pool-Zobel et al., 1997; Rock et al., 1997; Sharoni et al., 1997; Stahl and Sies, 1996). Therefore the engineered plants of the present invention can be advantageously utilized as a source of such compounds, either as fresh or processed foods or as nutraceuticals.

Furthermore hp-2 mutants have high levels of flavonoids such as anthocyanins (Von Wettstein-Knowles, 1968), which are also considered to be excellent antioxidants and which exhibit in some cases antitumoral properties (Fotsis et al., 1997; Rice-Evans et al., 1997). Furthermore some flavonoids exhibit a role in plant protection against pathogenic agents and UV light irradiation (Shirley,1996).

Therefore the manipulation of TDET1 activity can be used to modify carotenoid and/or flavonoid content in several plant species (e.g., tomato, pepper, eggplant, soybean, grape, melon, rice, carrot, spinach, citrus, and pomaceae) for biotechnological uses in both the biomedical and agro-industrial sectors.

Furthermore the manipulation of TDET1 gene expression can be used to modify the anthocyanin and carotenoid content in ornamental species for the achievement of new colour variants (Griesbach, 1984).

In addition, because it has been recognized that a high content of carotenoids improves resistance to Norflurazon-type herbicides, a further application of the TDET1 gene is the production of transgenic plants by selection using herbicides rather than antibiotic compounds (Misawa et al., 1993).

Furthermore in the same plant it is possible to combine a modified TDET1 activity with mutations such as rin, nor and Nr, which interrupt the fruit ripening process, or with biosynthetic genes of the carotenoid biosynthesis pathway (Bartley and Scolnik, 1995), to obtain varieties exhibiting new qualitative characteristics for agro-industry.

The attainment of an hp mutant phenotype by means of a biotechnological approach can be carried out advantageously by means of the inhibition of TDET1 activity. Currently the best method for reducing gene expression is through the introduction, by gene transfer, of the antisense sequence of the same gene or part thereof under the control of appropriate regulatory sequences. The use of such techniques in plants has been carried out in several existing examples (Oeller et al., 1991; Penarrubia et al., 1992), but those skilled in the art will recognize that alternative techniques can be used, without departing from the scope of the present invention.

Furthermore, by using specific vectors such as, for example, but not limited to, pE8mGFP4, which contains regulatory sequences of the tomato E8 gene (FIG. 9) (Deikman and Fischer, 1988), the inactivation of the TDET1 gene can be specifically modulated in the tomato fruit. Those skilled in the art will recognize that other regulatory sequences, e.g., originating from the polygalacturonase gene (PG) (Nicholass et al., 1995), can be used in the place of the E8 gene promoter to obtain specific tissue modulation of TDET1 gene expression.

Within the scope of the present invention the term "light hypersensitive phenotype" means reduced plant growth associated with high levels of carotenoids and/or chlorophylls and/or flavonoids.

The term "protein or functional parts thereof, responsible for the light hypersensitive mutant phenotype" means an amino acid sequence which, if structurally or otherwise altered, induces a light hypersensitive phenotype in a plant.

Therefore one object of the present invention is a nucleic acid comprising a nucleotide sequence encoding a protein, or functional parts thereof, which, if modified, is responsible for the light hypersensitive mutant phenotype in *Solanum lycopersicum* plants, said phenotype including reduced plant growth associated with high levels of carotenoids and/or chlorophylls and/or flavonoids. Nucleic acids encoding proteins which are homologous to proteins of the Arabidopsis COP/DET/FUS family, which when modified result in a light hypersensitive phenotype, are within the scope of the present invention.

Preferably the nucleic acid comprises the nucleotide sequence encoding the TDET1 protein, or functional parts thereof. More preferably the nucleic acid comprises a nucleotide sequence encoding the protein having the amino acid sequence of SEQ ID No. 2 or functional portions thereof. More preferably the nucleic acid has a nucleotide sequence comprised in SEQ ID No. 1, more preferably from nt. 149 to nt. 1720. Alternatively the nucleic acid has a nucleotide sequence complementary to SEQ ID No. 1, or parts thereof.

In one aspect of the invention the nucleic acid of SEQ ID No. 1 comprises a mutation which is able to induce the light hypersensitive phenotype; preferably at least a C→T substitution in position 1640; alternatively the nucleic acid of SEQ ID No. 1 is deleted at least from nt. 1581 to nt. 1589.

A further object of the present invention is an expression vector including, under the control of an active and inducible plant promoter, the nucleic acid of the invention. Preferably the promoter is active only in some plant organs, more preferably in fruits. Preferred vectors are able to drive the transcription of an antisense RNA, for example pBIN-E8-HP2-AS1 and pBIN-E8-HP2-AS2.

A further object of the invention is the use of the vectors of the invention for producing transgenic plants which comprise the nucleic acid, under the control of specific regulating sequences, preferably in preselected plant organs. Plants can belong to pepper, eggplant, soybean, grape, melon, rice, carrot, spinach, citrus, pomaceae and ornamental species.

A further object of the invention is a transgenic plant, or parts thereof, achievable by transformation with the vectors of the invention. Plants can belong to pepper, eggplant, soybean, grape, melon, rice, carrot, spinach, citrus, pomaceae and ornamental species.

Plant genetic transformation techniques are known to those skilled in the art and comprise, but are not limited to transformation by Agrobacterium, electroporation, microinjection, or bombardment with DNA coated particles (Christou, 1996).

In a further aspect the invention includes a protein, or functional parts thereof, whose modification is responsible for the light hypersenstive phenotype in Solanum lycopersicum plants. Proteins homologous to the Arabidopsis COP/DET/FUS family are within the scope of the present invention, provided that, when modified, they result in a light hypersensitive phenotype. Preferably the protein comprises the amino acid sequence of SEQ ID No. 2 or parts thereof.

In one aspect of the invention the protein comprises a modification which is able to induce the light hypersensitive phenotype; preferably at least a modification in its C-terminal portion; more preferably a replacement of proline at position 498, most preferably serine as a substitute for proline; alternatively a deletion of at least one amino acid, preferably at least three amino acids, more preferably from aa. 478 to aa. 480 of SEQ ID No. 2.

The present invention will be described by reference to explanatory, but not limiting, examples, wherein reference will be made to the following figures:

FIG. 1. Phenotypes of wild type, hp-2, and hp-$2^j$ tomato seedlings grown in the presence or in the absence of light. a) Hypocotyl length of seedlings grown in the absence (Dark) and in the presence of light (Light). b) Content of anthocyanins in the hypocotyls (dashed bars) and in the cotyledons (empty bars) of seedlings grown in the light. Data represent average values from ten seedlings. Following a three day pre-germination period in darkness, seedlings were grown either in darkness (Dark) or in a 16 hour light, 8 hour dark photoperiod (Light) for 6 days.

FIG. 2. TDET1 (HP-2) cDNA nucleotide sequence (SEQ ID NO. 1). The sequence encoding the TDET1 protein is depicted in capital letters. The sequence of the RFLP CT151 marker covers nt. 830 to nt. 2000.

FIG. 3. Amino acid sequence of the TDET1 (HP-2) protein (SEQ ID No. 2). Amino acids are depicted in the standard one letter code for amino acids.

Figure 4:
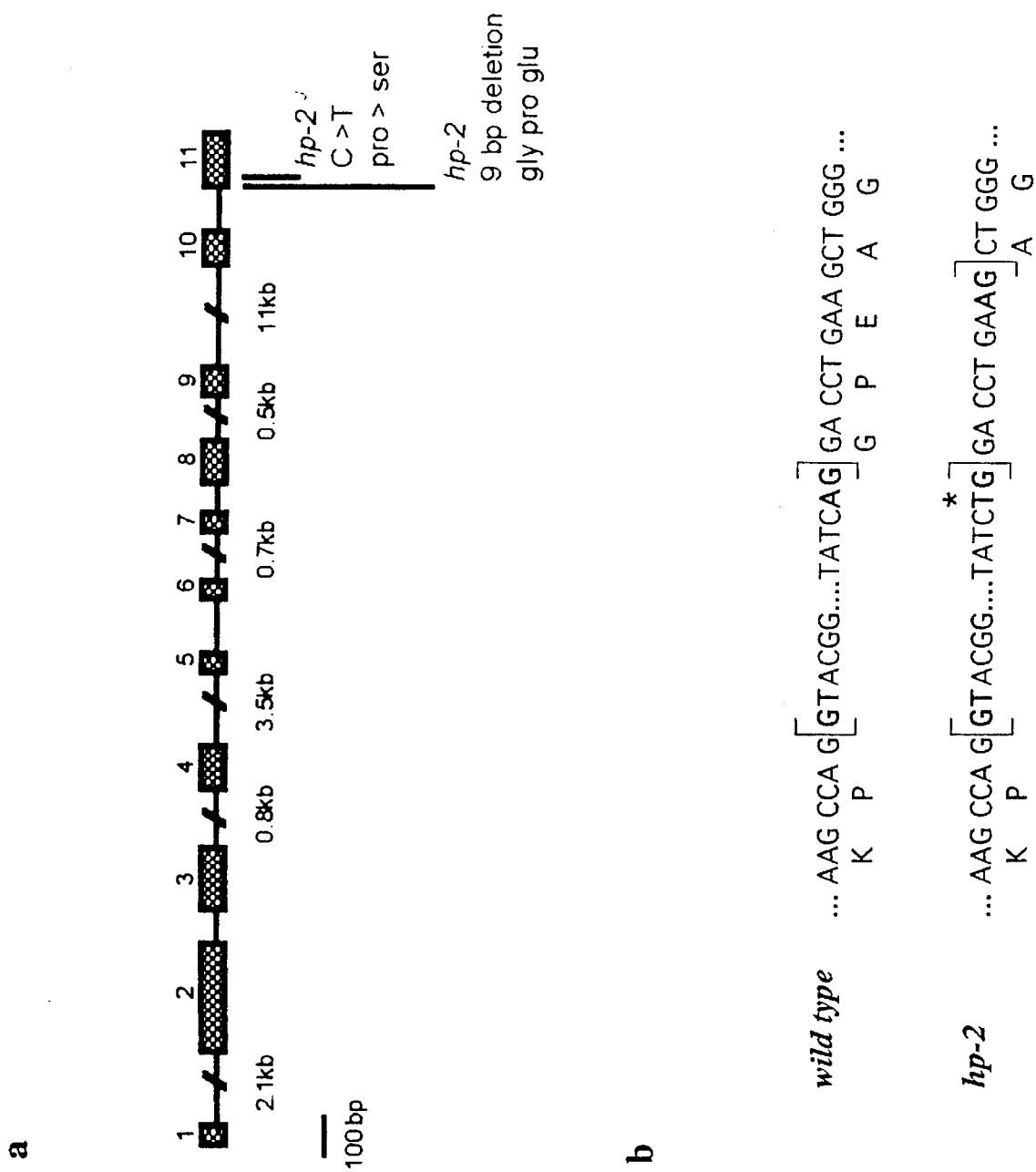

FIG. 4. Exon-intron structure of the tomato TDET1 (HP-2) gene and sites of mutations in hp-2 and hp-$2^j$ mutant alleles. Stippled boxes indicate exons. Exons correspond to the following sequences of SEQ ID No. 1 (FIG. 2): Exon 1: nt. 149 to nt. 220; Exon 2: nt. 221 to nt. 648; Exon 3: nt. 649 to nt. 877; Exon 4: nt. 877 to nt. 1012; Exon 5: nt. 1013 to nt. 1081; Exon 6: nt. 1082 to nt. 1138; Exon 7: nt. 1139 to nt. 1219; Exon 8: nt. 1220 to nt. 1384; Exon 9: nt. 1385 to nt. 1480; Exon 10: nt. 1481 to nt. 1580; Exon 11: nt. 1581 to nt. 1720; b) Donor and acceptor splice sites of intron 10 from the wild type and the hp-2 mutant. Brackets indicate splice sites, dots indicate internal intron sequence (not shown), and amino acids are shown in the one letter code. The asterisk in the hp-2 sequence denotes the site of the mutation.

FIG. 5. Alignment of the amino acid sequences of S. lycopersicum TDET1, Arabidopsis DET1, and deduced mammalian EST amino acid sequences with homology to DET1 (determined using Clustal method; Higgins and Sharp, 1988). The putative bipartite NLS is overlined. The amino acids missing in the hp-2 mutant are indicated with asterisks, and the amino acid substitution in hp-2i is denoted by a plus sign. The mammalian sequences are a compilation of derived amino acid sequences from mouse and human ESTs (GenBank accession numbers AA756238, AA236057, AA050184, and W64359). Boxed residues indicate conserved amino acids, dashes indicate arbitrary insertions.

Figure 6:
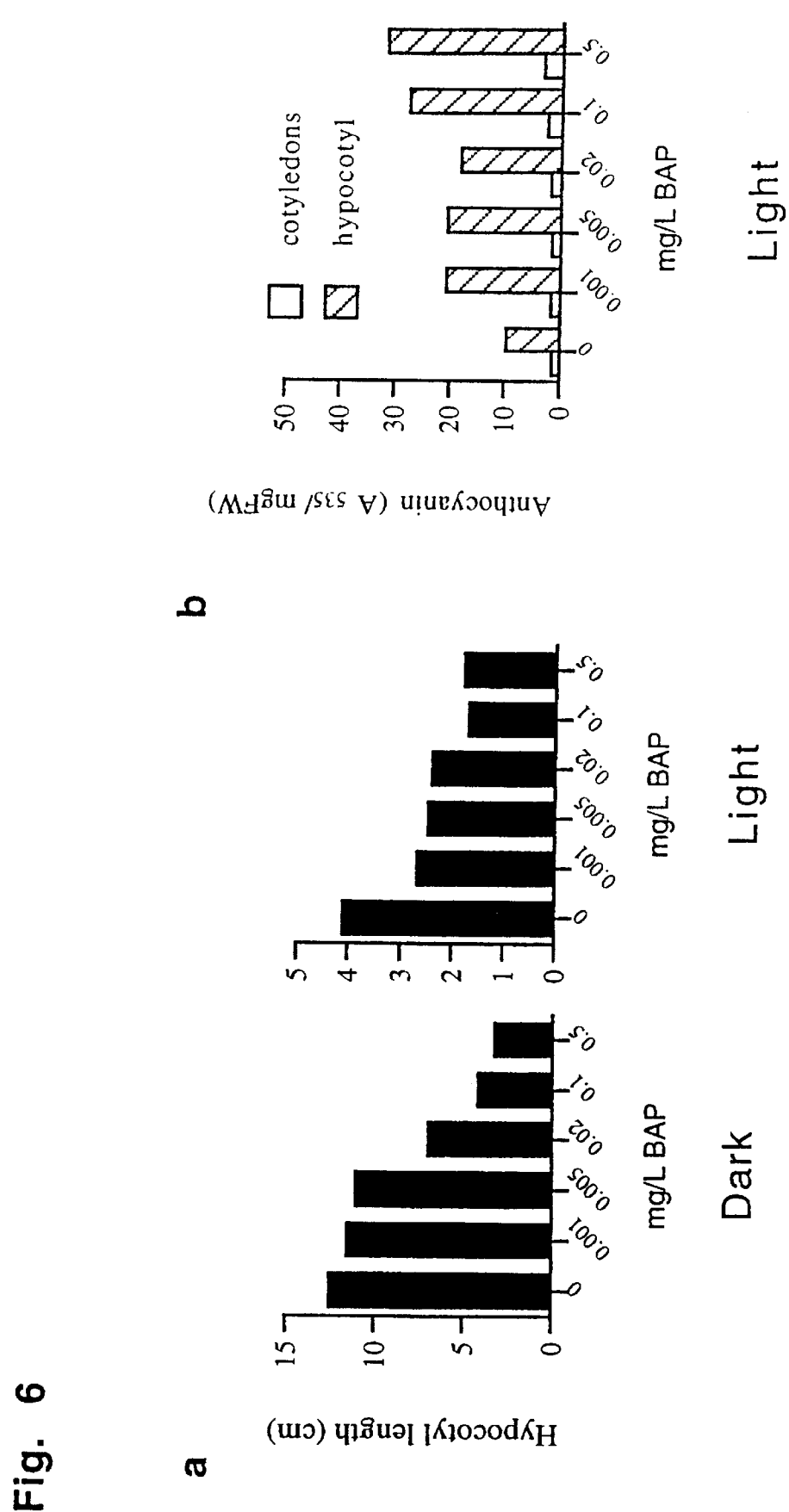

FIG. 6. Effect of cytokinins on wild type tomato seedlings.(a) and (b) Hypocotyl length (cm) and anthocyanin content (per mg fresh weight [FW]), respectively, of wild type tomato seedlings grown in the presence of 0, 1, 5, 20, 100, and 500 $\mu$g/L benzoaminopurine. Seedlings were grown at 25° C. for 5 days in absolute darkness (Dark) or in a 16-hr light 8-hr dark photoperiod (Light). In (a) values are the mean of 10 seedlings. Highly similar results were obtained with the cytokinin zeatin (data not shown).

Figure 7:
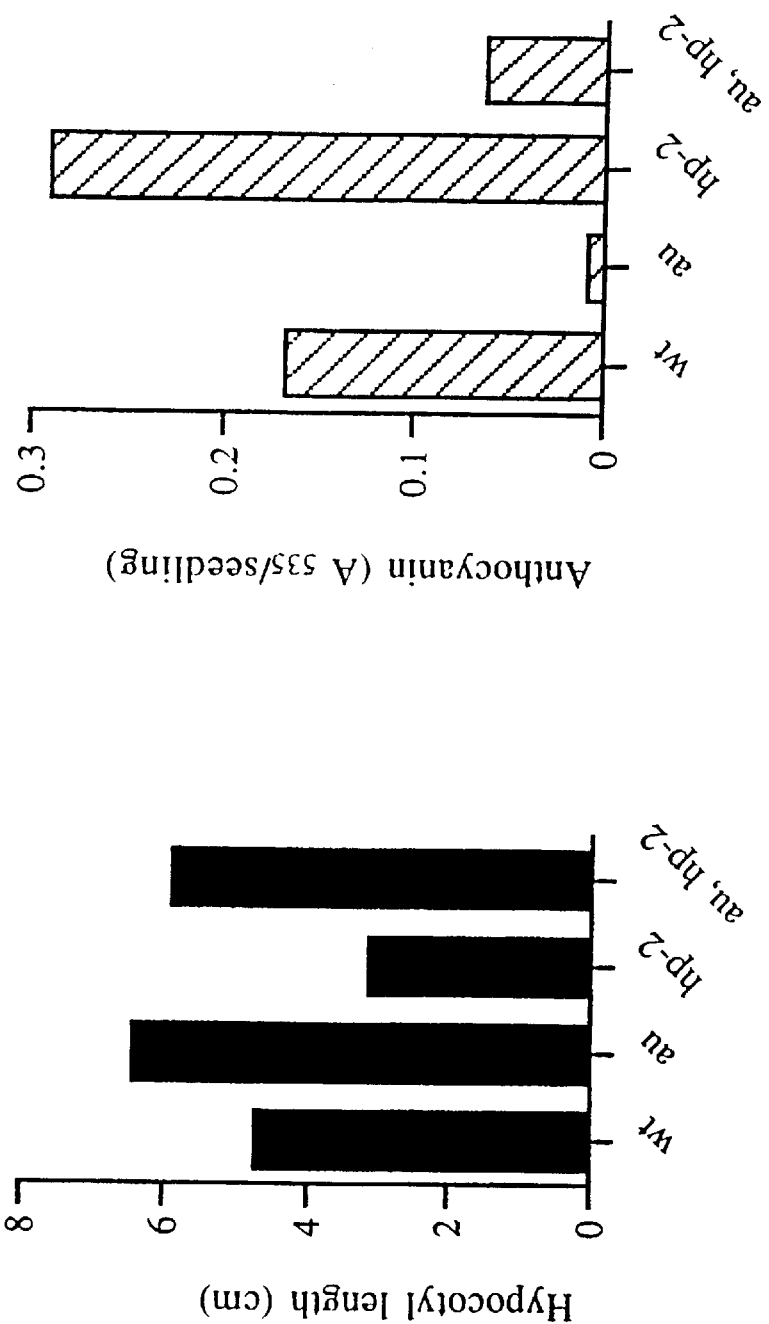

FIG. 7. Phenotype of the au hp-2 double mutant phenotype. Hypocotyl length (cm) and anthocyanin accumulation (per seedling) in wild type, au, hp-2, and the au hp-2 double mutant are shown. Seedlings were grown at 25 ° C. for 6 days in a 16-hr light 8-hr dark photoperiod. Values are the mean of 15 seedlings, and the experiments were repeated three times.

Figure 8:
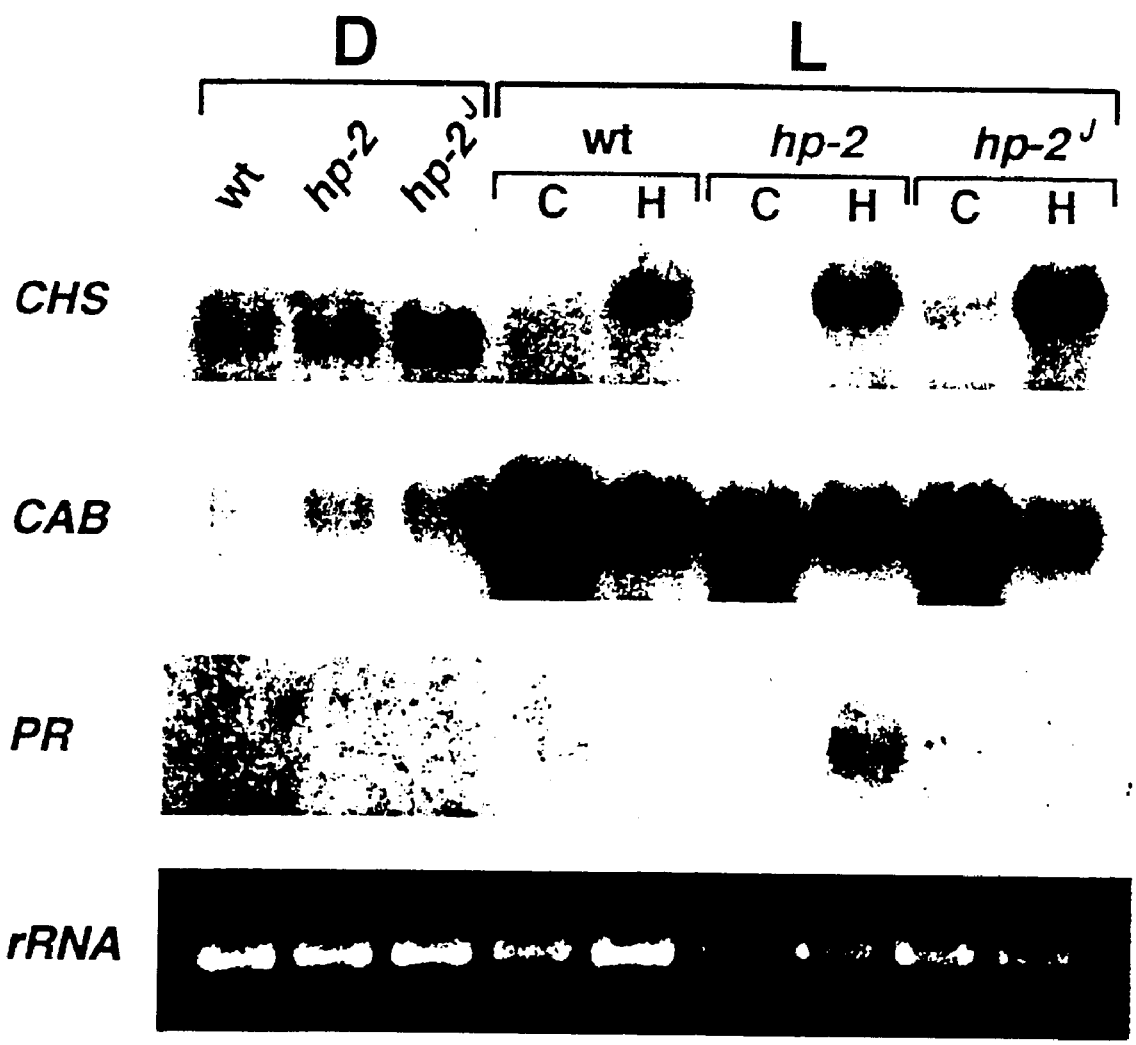

FIG. 8. Gene expression in wild type, hp-2, and hp-$2^j$ seedlings. Seedlings were grown at 25° C. for 5 days in absolute darkness (D), followed by 2 days in continuous white light (L). The RNAs were extracted from whole seedlings (dark) or from cotyledons (C) and hypocotyls (H) (light). Modifications in gene expression in hp-2 and hp-$2^j$ seedlings compared with wild type seedlings (wt) are shown to be principally light-dependent. Ten microgram samples of total RNA were loaded on gels and analyzed for expression of CHS1 (CHS), CAB6 (CAB), PR1-1b1 (PR) genes following RNA gel blotting. 30S rRNA is shown as a control for loading.

Figure 9:
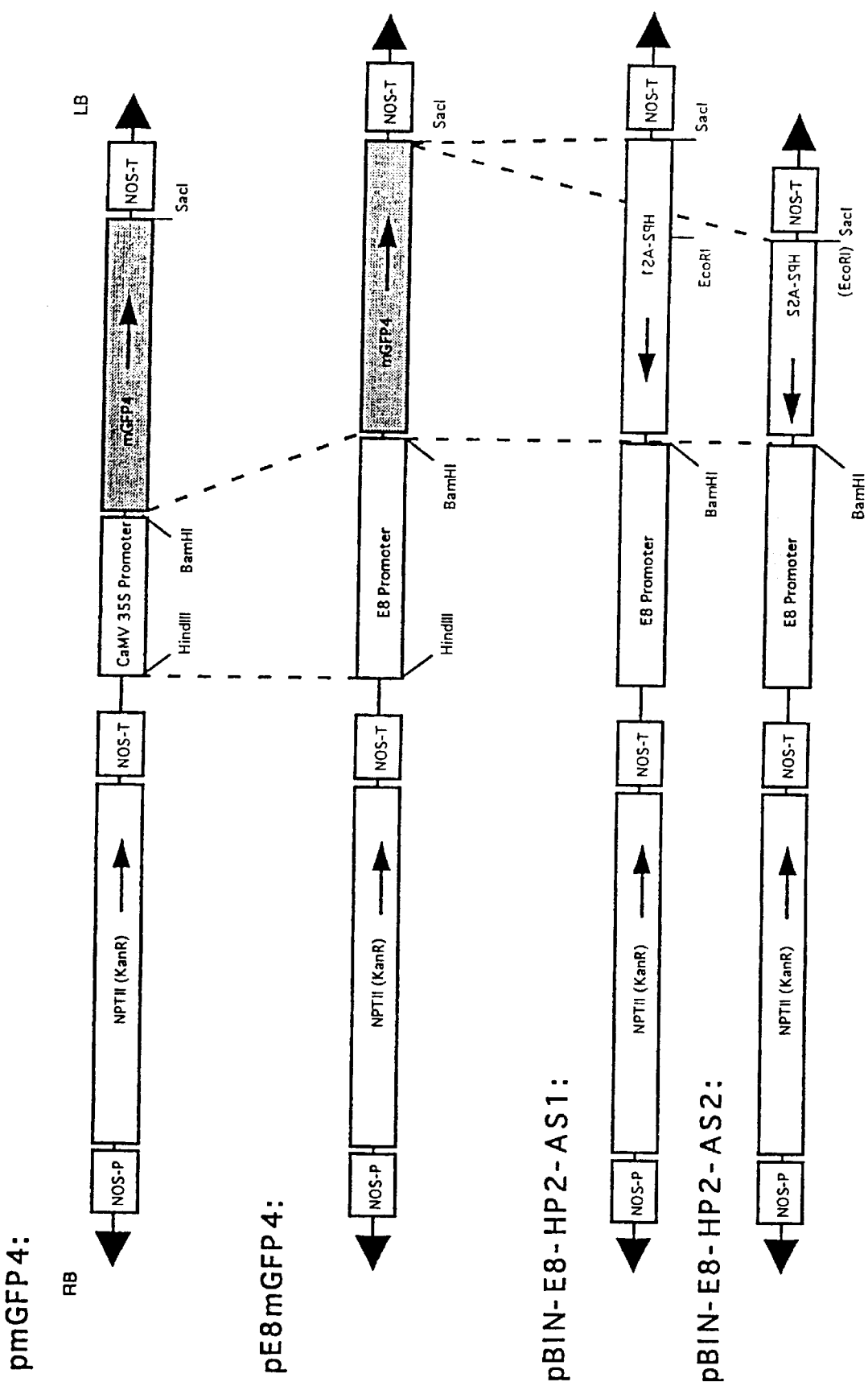

FIG. 9. Binary plasmids to be transferred to plants.

MATERIALS AND METHODS

Plant Material and Growth Conditions

The hp-2 and hp-$2^j$ exaggerated photoresponse mutants, the au hp-2 double mutant, and the corresponding wild type tomato seeds (Solanum lycopersicum cv Money Maker) were kindly provided by R. E. Kendrick and M. Koornneef (Wageningen Agricultural University, the Netherlands). Seeds were surface sterilized and directly sown in magenta boxes (Sigma) containing 4.3 g/L Murashige-Skoog salts (Sigma) and 0.8% agar. After 2 days pregermination in darkness, seedlings were grown at 25° C. either in a 16 hour light, 8 hour dark photoperiod or in continuous dark, as appropriate. For cytokinin treatment, seeds were sown in the presence of different concentrations of benzylaminopurine (Sigma).

Anthocyanin Assay

Anthocyanins were extracted from cotyledons, hypocotyls, and whole seedlings with 0.5 mL acidified (1% HCl) methanol for 48 hr in darkness with shaking. The extracts were separated by the addition of 0.4 mL of $H_2O$ and 1 mL of chloroform, followed by centrifugation for 5 min at 3,000 rpm. The absorbance of the upper phase was determined spectrophotometrically at 535 nm ($A_{535}$), and the anthocyanin content was calculated as ($A_{535}$)/mg fresh weight or ($A_{535}$)/seedling.

Carotenoid and Chlorophyll Assay

In order to determine the content of carotenoids and chlorophyll in the tomato fruit, pericarp sections of unripe (25 days after pollination) or ripe (50 days after pollination) fruit were weighed and incubated for 48 hours at 65° C. in DMSO (dimethyl sulfoxide) in the absence of light. The contents of carotenoids and chlorophylls were determined by HPLC and values are reported as µg/g fresh weight.

DNA and RNA Extraction

DNA and RNA extractions from leaf samples were carried out according to Dellaporta et al. (1983) and Verwoerd et al. (1989), respectively.

RNA gels (10 µg per lane) were blotted onto Hybond N+membranes (Amersham) and hybridized with random primed probes (see below). Hybridization was performed for 24 hr at 50° C. in phosphate buffer (7% SDS, 0.5M $Na_2HPO_4$, pH 7.2, 1 mM EDTA), followed by 20-min washes in 4 mM $NaPO_4$ pH 7.2, 1% SDS, and 1 mM EDTA. Probes were the tomato chalcone synthase gene CHS1 (O'Neill et al., 1990), chlorophyll a/b binding protein gene CAB6 (Piechulla et al., 1991) and pathogenesis-related protein gene PR-1b1 (Tornero et al., 1997). All RNA gel blots were repeated at least twice and using different samples.

Isolation and Sequence of Genomic Clones, cDNAs and PCR Products

5' amplification of cDNA was performed using the RACE system (Gibco/BRL) on total tomato leaf RNA with the oligonucleotide 5'-CATCAACACTGCCAAAC-3' (SEQ ID No. 3), derived from the CT151 RFLP marker sequence. A 0.8-kb Polymerase Chain Reaction (PCR) product, containing the 5' end of the TDET1 cDNA, was obtained after two different amplification reactions with Taq1 polymerase (Perkin Elmer) using two CT151-derived nested primers: 5'-GAAAGCAGCCGTTGCT-3' (SEQ ID No. 4) and 5'-AGTTCATCATCTTCACGGC-3' (SEQ ID No. 5), with the provided anchor primer (Gibco/BRL) The 0.8 kb PCR fragment was directly sequenced on both strands with thermosequenase (Amersham).

Total cDNA from wild type tomato (cv. Money Maker) and the corresponding hp-2 and hp-2$^j$ mutants were obtained by reverse transcription using avian myeloblastosis virus reverse transcriptase (Promega) of poly(A) mRNA isolated from leaves using oligo(dT) Dynabeads (Dynal). From these samples the TDET1 (HP-2) cDNA sequence was PCR amplified with the specific oligonucleotides: 5'-GTATGATTCACTAGTTTAATGCTGCTGAAAG-3' (SEQ ID No. 6) and 5'-CCCATACTAGTCGTCTTGGCACTCTATCAAG-3' (SEQ ID No. 7), using the Expand High Fidelity system (Boehringer Mannheim). Subsequently the amplification product was subcloned in pBluescript as a SpeI fragment and 4 independent clones were sequenced on both strands.

Tomato genomic libraries in λ-DASH and λ-FIXII (kindly provided, respectively, by Jim Giovannoni, Texas A&M University, College Station, Tex., and the Tomato Genome Center, Rehovot, Israel) were screened using standard methods (Sambrook et al., 1989) with a $^{32}$P-labelled CT151 fragment as a probe. Overlapping fragments from different recombinant phages were subcloned in pBluescript SK+ for sequencing of both strands.

The 5'-GAAGGTAATTTTATATTAAACATAGAATAGA-3' (SEQ ID No. 8) and 5'-GTGATTTCTAGGTTGATTTCAATCTAGA-3' (SEQ ID. No. 9) oligonucleotides were used to amplify the HP-2 gene 3' sequence from genomic DNA of the hp-2 mutant. The 1,300 bp amplification product was directly sequenced with the primer 5'-CAAATCGGTAACATAT-3' (SEQ ID No. 10) using a Thermosequenase kit (Amersham).

Binary Plasmids for Plant Transformation

DNA fragments containing the tomato fruit-specific E8 promoter (Deikman and Fischer, 1988) were PCR amplified from *S. lycopersicum* total DNA with the following nucleotides:
5'-GGGGAAGCTTTTTCACGAAATCGGCCCTTA-3' (SEQ ID No. 11) and 5'-CCCGGATCCTTCTTTTGCACTGTGAATGATTAG-3' (SEQ ID No. 12). The 1.2 kb amplification products were subcloned as HindIII-BamHI fragments in the binary expression vector pmGFP4, derived from pBI121 (Bevan, 1984; Jefferson et al., 1987; Haseloff et al., 1997) in place of the 35S promoter, obtaining the plasmid pE8mGFP4. The mGFP4 gene was then excised and the inverted or complementary sequence of the HP-2 gene, or parts thereof, was inserted, as BamHI-SacI fragments, obtaining the plasmid pBIN-E8-HP2-AS1 and pBIN-E8-HP2-AS2, respectively (FIG. 9).

Results hp-2 Mutant Phenotypes hp-2 mutant seedlings exhibited an exaggerated light response with respect to wild type seedlings. Particularly, hypocotyl length was reduced (FIG. 1a) and the content of anthocyanin pigments in the cotyledons was higher than in the wild type (FIG. 1b). Such phenotypes were strictly dependent on the presence of light; in fact in the absence of light the length of hypocotyl was not considerably different to the wild type (FIG. 1a) and anthocyanins were not produced (data not shown). The hp-2$^j$ mutant exhibited a stronger phenotype than the hp-2 mutant, with reference both to hypocotyl length and the content of anthocyanins (FIG. 1).

Fruits obtained from plants of hp-2 and hp-2$^j$ mutants also exhibited exaggerated light responses. In the unripe fruits from hp-2 and hp-2$^j$ mutants the content of chlorophyll was about five times higher than in fruits from wild-type plants, whereas in mature fruits the total content of carotenoids was about twice that of fruits from wild-type plants (Table 1).

TABLE 1

Chlorophyll and carotenoid content of tomato fruits from wild type, hp-2 and hp-2$^j$ mutants.

| Genotype | Total Chlorophylls (ripe fruit) µg/g fresh weight | Total Carotenoids (unripe fruit) µg/g fresh weight |
|---|---|---|
| wild type (Money Maker) | 20 | 60 |
| hp-2 | 90 | 124 |
| hp-2$^j$ | 115 | 137 |

The Phenotype of the Tomato hp-2 Mutant is Caused by Mutation in DET1

The hp-2 mutation has been mapped previously using restriction fragment length polymorphism (RFLP) analyses of a segregating population derived from a cross between the hp-2 mutant (*S. lycopersicum*) and *S. pennellii*. Mapping data with a second backcross (BC-2) population indicated a position close to the centromere of chromosome 1, within a cluster of several RFLP markers (Balint-Kurti et al., 1995; Van Tuinen et al., 1997; Broun and Tansksley, 1996). The authors of the present invention have found that the CT151 RFLP marker (Tanksley et al., 1992), included in this cluster, had high homology with the Arabidopsis DET1 gene, mutations in which were previously identified as causing the deetiolated phenotype of det1 mutants.

Comparison of CT151 with Arabidopsis DET1 revealed that CT151 has homology to the 3' end of DET1. The authors of the present invention isolated a full-length cDNA encoding TDET1 using 5' rapid amplification of cDNA ends (Loh et al., 1989). Subsequently, the TDET1 gene was isolated from genomic libraries in λ-DASH and λ-FIXII. Alignment of the TDET1 cDNA and genomic sequences revealed the presence of 10 introns, which is similar to the number found in Arabidopsis (FIG. 4a). Nine introns are located in the same positions as those of the Arabidopsis DET1 gene, whereas intron 2 of TDET1 is not present in the Arabidopsis homolog (FIG. 4a) (Pepper et al., 1994). Comparative protein sequence analysis between Arabidopsis DET1 and TDET1 show 81.3% similarity and 74.8% identity (FIG. 5). No major differences are present between the sequences, except for a small deletion of 16 amino acids at the centre of TDET1, suggesting that the tomato and Arabidopsis genes are true homologs. A DET1 homolog is not present in the yeast genome or in any prokaryotic genome sequenced to date (data not shown). However, mouse and human expressed sequence tags (ESTs) with homology to DET1 have been identified (FIG. 5), as well as a Drosophila homolog.

Considering the presence of a nuclear localisation signal (NLS) (Robbins et al., 1991) in the Arabidopsis DET1 amino acid sequence, and observing that the DET1-GUS chimeric protein is localised in the nucleus (Pepper et al., 1994), DET1 in Arabidopsis may be responsible for the transcriptional repression of photomorphogenesis in the absence of light. Considering the homology with HP-2 it is possible for the latter to have an analogous function in tomato. The TDET1 protein has been found to be localized in the nucleus (data not shown).

TDET1-encoding cDNAs from the wild type, and hp-2 and hp-$2^j$ mutants were amplified with specific primers from leaf mRNA. Amplified fragments were subcloned in pBluescript and 4 independent clones were sequenced on both strands. In hp-2 the authors identified a substitution involving T in the place of C in exon 11 (nt. 1640) that causes a replacement of proline by serine in the protein C-terminal region (aa. 498) (FIG. 4a). In the hp-2 mutant the authors identified an alternative splicing site for intron 10, which causes a three amino acid deletion (Gly, Pro, Glu) at the start of exon 11, in the second NLS domain of the protein (aa. 478–480) (FIG. 4a). To find the mutation site which was responsible for the alternative splicing, the authors sequenced the 3' end of the TDET1 gene from the hp-2 mutant, using a fragment obtained by PCR amplification of genomic DNA. A replacement of AG by TG in the consensus 3' splice junction of intron 10 was identified (FIG. 4b). These results demonstrate that the "high pigment" phenotype of the hp-2 and hp-$2^j$ tomato mutants is caused by mutation of the TDET1 gene mutation.

Sequencing of the TDET1 cDNAs derived from the hp-2 mutant showed that the mutation produces two different splicing products from intron 10 (FIG. 4b), suggesting the presence of a limited amount of wild-type TDET1 protein and that the hp-2 mutant is not an inactive allele. This is consistent with the observation that the hp-2 mutant allele is weaker than the hp-$2^j$ allele (FIG. 1 and Table 1). Whether the hp-$2^j$ mutation is null awaits further analysis, although the mutated proline residue in the hp-$2^j$ mutant is conserved in both the plant sequences. However, because the hp-2 mutation is situated in the C-terminal domain of TDET1, as is the mutation in the Arabidopsis det1-5 mutant allele, which has a clearly de-etiolated phenotype (Pepper et al., 1994), it is apparent that the hp-2 mutant phenotypes are not comparable with the det1 mutant phenotype in Arabidopsis. Furthermore, clearly weak alleles of det-1 in Arabidopsis, eg. det1-1, display visible dark phenotypes.

Comparison of Tomato hp-2 and Arabidopsis det1 Mutants

As is clear from the results presented, hp-2 mutants are phenotypically different from det1 mutants. Most conspicuously they do not display dark phenotypes, such as reduced hypocotyl length, opened apical hooks, or enlarged cotyledons, whereas these were selection criteria for the isolation of det and cop in Arabidopsis (Chory et al., 1989; Deng et al., 1991). Conversely, det1 mutants can even develop true leaves and floral buds in prolonged darkness. No such phenotypes can be observed in hp tomato seedlings grown in the dark.

Arabidopsis det1 mutants are also characterized by high level expression of light-regulated genes such as CHS and CAB in the dark, whereas in the light, CHS and CAB gene expression are similar to that observed in wild-type plants (Chory et al., 1989). To examine the effects of hp-2 and hp-$2^j$ mutations on gene expression, the authors have performed RNA gel blot analysis of light-regulated gene expression using CHS and CAB gene fragments as probes. In agreement with the weak phenotypes of hp-2 and hp-$2^j$ mutant seedlings grown in darkness, no dramatic alteration of CHS and CAB gene expression was observed. Nonetheless, CHS and CAB mRNA levels were slightly higher in the hp-$2^j$ allele when compared with hp-2 and wild-type seedlings (FIG. 8). Interestingly, CHS mRNA appeared to be of a slightly smaller size than that found in light-grown material, perhaps indicating a differential light-dependent splicing. Consistent with the exaggerated photoresponsiveness of hp-2 and hp-$2^j$ mutants, CHS mRNA levels were significantly enhanced compared with wild-type seedlings following light irradiation for 48 hr (FIG. 8). hp-$2^j$ seedlings contained higher expression levels of CHS than hp-2, and CHS mRNA was particularly abundant in hypocotyls. In contrast to CHS, CAB mRNA levels were higher in cotyledons than in hypocotyls, and were slightly lower in light-exposed hp-2 and hp-$2^j$ mutant seedlings when compared to the wild type (FIG. 8). In summary therefore, in tomato hp-2 mutants dark expression of CHS and CAB genes is only very slight and deregulation of gene expression is essentially light-dependent. This is in strong contrast to the CHS and CAB gene deregulation characteristics of Arabidopsis det1 mutants (Pepper et al., 1994).

det1 seedlings have been also reported to display a strongly enhanced expression of stress-related genes such as those encoding pathogenesis-related (PR) proteins and glutathione reductase (Mayer et al., 1996) To examine whether this was also the case in hp-2 and hp-$2^j$ mutants, RNA gel blots were hybridized with a probe encoding tomato PR-1b1 (Tornero et al., 1997). Although hypocotyls of hp-2 seedlings reproducibly displayed PR-1b1 gene expression at slightly higher levels compared to wild-type seedlings, this effect was very weak compared to that observed in Arabidopsis det1 mutants and has never been observed in hp-$2^j$ mutants (FIG. 8).

Despite these above-mentioned differences, plastid development in darkness in the cotyledons of hp-2 and hp-$2^j$ seedlings was found by the authors to be similar to that observed in Arabidopsis det1 mutants (data not shown; Chory et al., 1989).

Cytokinin can Phenocopy the hp Mutant

Previous observations in Arabidopsis have shown that a det1 phenotype can be phenocopied by the exogenous application of cytokinin (Chory et al., 1994).

To determine the effects of cytokinin treatment in tomato, the authors treated wild-type seedlings with different concentrations of cytokinin in the dark and in the light (FIG. 6). Cytokinin was found not to phenocopy a det1 mutation in tomato. In dark-grown seedlings, although hypocotyls are shorter in the presence of cytokinin, apical hook opening, cotyledon expansion, and anthocyanin biosynthesis were not observed (FIG. 6), even after prolonged periods (up to three weeks) (data not shown). However, in the light, cytokinin can phenocopy the hp mutation: seedlings displayed shorter and thicker hypocotyls and accumulated high levels of anthocyanin (FIG. 6).

These results therefore indicate that at least as far as the effects of cytokinin are concerned, the hp mutation in tomato is equivalent to the det1 mutation in Arabidopsis. Such a supposition is consistent with the fact that no constitutive de-etiolated mutants have heretofore been identified in tomato and CHS gene expression and consequent biosynthetic build-up of anthocyanin pigments is strictly dependent on the light, whereas in Arabidopsis anthocyanins can be produced also in the absence of light (Mustilli and Bowler, 1997).

Double Mutant Analyses

Double mutant analysis with det1 and phytochrome-deficient mutants in Arabidopsis indicate that the det1 mutation is completely epistatic to photoreceptor mutations (Chory, 1992). This has been interpreted as meaning that DET1 acts downstream of phytochrome. To determine the relationship between TDET1 and phytochrome function, we examined the effects of the hp-2 mutation in the aurea mutant background, a phytochrome chromophore-deficient mutant (Terry and Kendrick, 1996). In contrast to its counterpart double mutant in Arabidopsis, au hp-2 is similar to the single mutant au. For example, hypocotyls are elongated and anthocyanin accumulation is limited (FIG. 7). Although in genetic terms this result therefore infers that au is epistatic to hp-2, the authors nonetheless consider it more likely that TDET1 acts downstream of phytochrome, as proposed for Arabidopsis, but that its activity as a negative regulator is strictly dependent upon the presence of active phytochrome. This requirement is clearly not observed in Arabidopsis (Chory, 1992). The small but significant reduction in hypocotyl length and the small increase in anthocyanin found in the au hp-2 double mutant compared with au (FIG. 7) is likely therefore to be a result of hypersensitivity caused by the hp-2 mutation towards the low amounts of functional phytochrome present in the au mutant, which is estimated to be about 3% wild-type levels (Adams et al., 1989; Parks et al, 1987). Therefore the hp-2 phenotype in tomato is strictly dependent on the presence of phytochrome, whereas in Arabidopsis the det1 mutation is independent of the presence or absence of functional photoreceptors.

The absence of de-etiolated mutants in tomato and the strict light- and phytochrome-dependence of the hp mutant phenotype may suggest that in tomato TDET1 function is either redundant or that the signal transduction pathways regulating its activity operate in different ways in the two plants (Mustilli and Bowler, 1997). Because by Southern analysis the authors have shown that in tomato, like in Arabidopsis (Pepper et al., 1994), only one DET1 homologous gene is present (data not shown), the latter hypothesis seems to be more likely.

Based upon the author's findings, it is likely that only a few key regulators will be found to be responsible for controlling light responses in all higher plants. Therefore it would be very interesting to clone other tomato genes encoding proteins homologous to COP/DET/FUS and examine whether modification of their activity also results in light hypersensitive phenotypes.

Binary Plasmids for Modulation of TDET1 Activity

In order to generate tomato plants with an hp-2 phenotype specifically in the fruit, the authors constructed plasmids which are able to produce the TDET1 antisense RNA sequence, or portions thereof, only in the fruit by using the regulatory sequences of the tomato E8 gene (FIG. 9).

BIBLIOGRAPHY

Adamse, P., et al. (1989) Photochem. Photobiol. 50, 107–111.
Balint-Kurti, P. J., Jones, D. A., and Jones, J. D. G. (1995) Theor. Appl. Genet. 90, 17–26.
Bartley, G. E. and Scolnik, P. A. (1995) Plant Cell 7, 1027–1038.
Bevan, M. W. (1984) Nucl. Acids Res. 12, 8711–8721.
Bowler, C. and Chua, N-H. (1994) Plant Cell 6, 1529–1541.
Boylan, M. T. and Quail, P. H. (1989) Plant Cell 1, 765–773.
Broun, P. and Tanksley, S. D. (1996) Mol. Gen. Genet. 250, 39–49.
Chamovitz, D. A. and Deng, X.-W. (1996) Crit. Rev. Plant Sci. 15, 455–478.
Chory, J (1992) Development, 115, 337–354.
Chory, J., et al. (1996) Proc. Natl. Acad. Sci. USA 93, 12066–12071.
Chory, J., et al. (1989) Cell 58, 991–999.
Chory, J. and Peto, C. (1990) Proc. Natl. Acad. Sci. USA 87, 8776–8780.
Chory, J., et al. (1994) Plant Physiol. 104, 339–347.
Chistou, P. (1996) Trends Plant Sci., 1, 423–431.
Clack., T., Mathews, S. and Sharrock, R. A. (1994) Plant Mol. Biol. 25, 413–427.
Deikman, J. and Fischer, R. L. (1988) EMBO J. 7, 3315–3320.
Dellaporta, S. L., Wood, J. and Hicks, J. B. (1983) Plant Mol. Biol. Reporter 1, 19–21.
Deng, X.-W., Caspar, T. and Quail, P. H. (1991) Genes & Dev. 5, 1172–1182.
Fotsis, T., et al. (1997) Cancer Res. 57, 2916–2921.
Giles, G. and Ireland, P. (1997) Int. J. Cancer 10, 13–17.
Griesbach, R. J. (1984) J. Hered. 75, 145–147.
Haseloff, J., et al. (1997) Proc. Natl. Acad. USA 94, 2122–2127.
Higgins, D. G., and Sharp, P. M. (1988) Gene 73, 237–244.
Hoffmann, I and Weisburger, J. H. (1997) Cancer Epidemiol. Biomarkers Prev. 6, 643–645.
Jefferson, R. A., Kavanagh, T. A. and Bevan M. W. (1987) Embo J. 6, 3901–3907.
Kendrick, et al. (1994) Biochem. Soc. Symp. 60, 249–256.
Kerckhoffs, L. H. J., et al. (1997) J. Plant Physiol. 50, 578–587.
Loh, E.Y., et al. (1989) Science 243, 217–220.
Mayer, R., Raventos, D. and Chua, N.-H. (1996) Plant Cell 8, 1951–1959.
Millar, A. J., McGrath, R. B. and Chua, N.-H. (1994) Annu. Rev. Genet. 28, 325–349.
Misawa, N., et al. (1993) Plant J. 4, 833–840.
Mustilli, A. C. and Bowler, C. (1997) EMBO J. 16, 5801–5806.

Nicholass, F. J., et al. (1995) Plant Mol. Biol. 28, 423–435.
Oeller, P. W., et al. (1991) Science 254, 437–439.
O'Neill, S. D., et al. (1990) Mol. Gen. Genet. 224, 279–288.
Pappalardo, G, et al. (1997) Eur. J. Clin. Nutr. 51, 661–666.
Parks, B. M., et al. (1987) Plant. Mol. Biol. 9, 97–107.
Penarrubia, L., et al. (1992) Plant Cell 4, 681–687.
Pepper, A., et al. (1994) Cell 78, 109–116.
Peters, J. L., et al. (1989) J. Plant Physiol. 134, 661–666.
Piechulla, B., et al. (1991) Mol. Gen. Genet. 230, 413–422.
Pool-Zobel, B. L., et al. (1997) Carcinogenesis 18, 1847–1850.
Reynard, G. B. (1956) Tomato Genet. Coop. Report 6, 22.
Rice-Evans, C. A., Miller, N. J. and Paganga, G. (1997) Trends Plant Sci. 2, 152–159.
Robbins, J., et al. (1991) Cell 64, 615–623.
Rock, C. L., et al. (1997) Cancer Epidemiol. Biomarkers Prev. 6, 617–623.
Sambrook, J., Fritsch, E. F. and Maniatis, T. (1989) Molecular Cloning: A Laboratory Manual. (Cold Spring Harbour, N.Y., Cold Spring Harbor Laboratory Press).
Sharoni, Y., et al. (1997) Cancer Detect. Prev. 21, 118–123.
Sharrock, R. A. and Quail, P. H. (1989) Genes & Dev. 3, 1745–1757.
Shirley, B. W. (1996) Trends Plant Sci. 1, 377–382.
Soressi, G. P. (1975) Tomato Genet. Coop. Report 25, 21–22.
Stahl, W. and Sies, H. (1996) Arch. Biochem. Biophys. 336, 1–9.
Szekeres, M., et al. (1996) Cell 85, 171–182.
Tanksley, S.D., et al. (1992) Genetics, 132, 1141–1160.
Terry, M. J., and Kendrick, R. E. (1996) J. Biol. Chem. 271, 21681–21686.
Thompson, A. E. (1995) Science 121, 896–897.
Tornero, P., et al. (1997) Mol. Plant Microbe Interact. 10, 624–634.
Van Tuinen, A., et al. (1997) Theor. Appl. Genet. 94, 115–122.
Verwoerd, T. C., Decker, B. M. and Hoekema, A. (1989) Nucl. Acids Res. 17, 2362.
von Armin, A. and Deng, X.-W. (1996) Annu. Rev. Plant Physiol. Plant Mol. Biol. 47, 215–243.
Von Wettstein-Knowles, P. (1968) Hereditas 60, 318–346.
Whitelam, G. C. and Harberd, N. P. (1994) Plant, Cell and Environ. 17, 615–625.
Yen, H. C., et al. (1997) Theor. Appl. Genet. 95, 1069–1079.

What is claimed is:

1. An isolated nucleic acid or its complement encoding a TDET1 (HP-2) protein, said protein having the amino acid sequence set forth in SEQ ID NO. 2.

2. The isolated nucleic acid according to claim 1, wherein said nucleic acid has the nucleotide sequence set forth in SEQ ID NO:1, or its complement.

3. The isolated nucleic acid according to claim 1, comprising the nucleotide sequence of nucleotides 149 to 1720 in SEQ ID NO:1, or its complement.

4. An isolated nucleic acid coding for a mutated form of the nucleotide sequence set forth in SEQ ID NO:1, or its complement, wherein said mutated form comprises a nucleotide change selected from the group consisting of C to a T at nucleotide 1640 of SEQ ID NO:1, and a deletion of nucleotides 1581 to 1589 of SEQ ID NO:1.

5. The isolated nucleic acid according to claim 4, wherein said mutant comprises a change of C to a T at nucleotide 1640 in SEQ ID NO:1.

6. The isolated nucleic acid according to claim 4, wherein said mutant comprises a deletion of nucleotides 1581 to 1589 in SEQ ID NO:1.

7. An expression vector comprising the nucleic acid according to claim 1 under the control of a promoter that is active in plants.

8. Vector according to claim 7 wherein said promoter is selectively active only in selected plant organs.

9. The vector according to claim 8 wherein said plant organ is a fruit.

10. Vector according to claim 7 which is able to control the transcription of an antisense RNA.

11. An expression vector comprising the nucleic acid according to claim 2 under the control of a promoter that is active in plants.

12. An expression vector comprising the nucleic acid according to claim 3 under the control of a promoter that is active in plants.

13. An expression vector comprising the nucleic acid according to claim 5 under the control of a promoter that is active in plants.

14. An expression vector comprising the nucleic acid according to claim 6 under the control of a promoter that is active in plants.

15. The vector according to claim 11, wherein said promoter is selectively active only in selected plant organs.

16. The vector according to claim 12, wherein said promoter is selectively active only in selected plant organs.

17. The vector according to claim 13, wherein said promoter is selectively active only in selected plant organs.

18. The vector according to claim 14, wherein said promoter is selectively active only in selected plant organs.

19. The vector according to claim 15, wherein said plant organ is a fruit.

20. The vector according to claim 16, wherein said plant organ is a fruit.

21. The vector according to claim 17, wherein said plant organ is a fruit.

22. The vector according to claim 18, wherein said plant organ is a fruit.

23. Vector according to claim 7 which is able to control the transcription of an antisense RNA.

24. Vector according to claim 11 which is able to control the transcription of an antisense RNA.

25. Vector according to claim 12 which is able to control the transcription of an antisense RNA.

26. Vector according to claim 13 which is able to control the transcription of an antisense RNA.

27. Vector according to claim 14 which is able to control the transcription of an antisense RNA.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 2000 base pairs
      (B) TYPE: nucleic acid
      (C) STRANDEDNESS: single
      (D) TOPOLOGY: linear (ii) MOLECULE TYPE: cDNA to mRNA (ix) FEATURE:
      (A) NAME/KEY: CDS
      (B) LOCATION:149..1720

(xi) SEQUENCE DESCRIPTION: SEQ ID NO: 1:

```
CTTCCCTCTT AGACTTTATC GATCCTAATT CGAGCCCTCC TTTTTTCAAT CAATTATCAA        60

TTTAGTCCTA CTGCGATTTT GATATGTATG ATTCACAATT TTAATGCTGC TGAAAGCAAT       120

TATATAAAAG CTGAAACATT TTGCACTG ATG TTC AAA ACT AAC AAT GTT ACC          172
                                Met Phe Lys Thr Asn Asn Val Thr
                                  1               5

GCC AGG CTT TTT GAG CGC CAG ATT TGC ACC CCT GCT CCT GGC ACC AGC         220
Ala Arg Leu Phe Glu Arg Gln Ile Cys Thr Pro Ala Pro Gly Thr Ser
    10              15                  20

ATC CAT CGT GCC AGA AGA TTT TAT GAG AAC GTT GTA CCA AGT TAT ACC         268
Ile His Arg Ala Arg Arg Phe Tyr Glu Asn Val Val Pro Ser Tyr Thr
 25                  30                  35                  40

ATA TAC GAT GTT GAA TGT CCC GAC CAT TCA TTT CGC AAG TTC ACG GAT         316
Ile Tyr Asp Val Glu Cys Pro Asp His Ser Phe Arg Lys Phe Thr Asp
                 45                  50                  55

GAC GGT CTA TAT TTT GTA AGT TTC AGC CGA AAC CAT CAG GAT CTG GTT         364
Asp Gly Leu Tyr Phe Val Ser Phe Ser Arg Asn His Gln Asp Leu Val
             60                  65                  70

GTT TAT AGA CCA ACA TGG CTG ACA TTT TCC TGC AAA GAA GAA GAT TGT         412
```

-continued

```
                Val Tyr Arg Pro Thr Trp Leu Thr Phe Ser Cys Lys Glu Glu Asp Cys
                             75                  80                  85

GAT ACT CAT GAT CTT CCT TTG AAA GCT AGA AAG TTT GAG AGC TTC TTC          460
Asp Thr His Asp Leu Pro Leu Lys Ala Arg Lys Phe Glu Ser Phe Phe
         90                  95                 100

ACA CAG TTG TAC AGT GTT ACT CTT GCT TCT AGT GGG GAA CTT ATA TGC          508
Thr Gln Leu Tyr Ser Val Thr Leu Ala Ser Ser Gly Glu Leu Ile Cys
105                 110                 115                 120

AAA GAT TTC TTT CTC TAT ATG GAG AGC AAC CAA TTT GGA CTC TTT GCA          556
Lys Asp Phe Phe Leu Tyr Met Glu Ser Asn Gln Phe Gly Leu Phe Ala
                125                 130                 135

ACT TCA ACT GCA CAA ATT CAT GAT GCA CCT CCT ACT GGA GGG GCA ATT          604
Thr Ser Thr Ala Gln Ile His Asp Ala Pro Pro Thr Gly Gly Ala Ile
            140                 145                 150

CAG GGA GTC CCT TCA GTT GAA AAA ATA ACT TTC CAC CTT TTG AGG TTG          652
Gln Gly Val Pro Ser Val Glu Lys Ile Thr Phe His Leu Leu Arg Leu
            155                 160                 165

GTG GAT GGA GCT ATA CTT GAC GAA AGG GTT TTC CAC AAT GAT TAT GTT          700
Val Asp Gly Ala Ile Leu Asp Glu Arg Val Phe His Asn Asp Tyr Val
        170                 175                 180

AAT TTG GCA CAT AGC ATT GGT GCT TTC TTG TAT GAT GAT TTG CTT GCT          748
Asn Leu Ala His Ser Ile Gly Ala Phe Leu Tyr Asp Asp Leu Leu Ala
185                 190                 195                 200

ATA GTG TCT CTT CGT TAT CAA AGA ATA CAC ATC CTT CAG ATC AGA GAT          796
Ile Val Ser Leu Arg Tyr Gln Arg Ile His Ile Leu Gln Ile Arg Asp
                205                 210                 215

TCT GGA GAT CTT GTT GAT GTA CGA GCA ATT GGG GAA TTC TGC CGT GAA          844
Ser Gly Asp Leu Val Asp Val Arg Ala Ile Gly Glu Phe Cys Arg Glu
            220                 225                 230

GAT GAT GAA CTT TTT CTC AAT TCC AAT TCC CAG GTG CTT GTA AAT CAT          892
Asp Asp Glu Leu Phe Leu Asn Ser Asn Ser Gln Val Leu Val Asn His
            235                 240                 245

GTT GGA AAT GGT TTT CAT CAT AGT CTG CCT CAA TCA GAA ACT TCT TTC          940
Val Gly Asn Gly Phe His His Ser Leu Pro Gln Ser Glu Thr Ser Phe
        250                 255                 260

CTG AGC GGT ATA AAG CAA CGG CTG CTT TCA TAT ATA TTT CGA GGT ATA          988
Leu Ser Gly Ile Lys Gln Arg Leu Leu Ser Tyr Ile Phe Arg Gly Ile
265                 270                 275                 280

TGG AAT GAA GCT GAC CAA ACC ATG AGA GTG CAG TGC CTG AAG AAG AAG         1036
Trp Asn Glu Ala Asp Gln Thr Met Arg Val Gln Cys Leu Lys Lys Lys
                285                 290                 295

TTT TAC TTC CAC TTT CAA GAT TAC ATT GAC TTG ATT ATC TGG AAG GTG         1084
Phe Tyr Phe His Phe Gln Asp Tyr Ile Asp Leu Ile Ile Trp Lys Val
            300                 305                 310

CAG TTT TTG GAC CGA CAT CAC CTG TTG ATC AAG TTT GGC AGT GTT GAT         1132
Gln Phe Leu Asp Arg His His Leu Leu Ile Lys Phe Gly Ser Val Asp
            315                 320                 325

GGT GGG GTA TCC CGA AAT GCT GAC ATC CAT CCT TCT TTT TTT GCT GTT         1180
Gly Gly Val Ser Arg Asn Ala Asp Ile His Pro Ser Phe Phe Ala Val
        330                 335                 340

TAC AAT ATG GAG ACT ACT GAA ATT GTT GCA TTT TAT CAG AAC TCA GCC         1228
Tyr Asn Met Glu Thr Thr Glu Ile Val Ala Phe Tyr Gln Asn Ser Ala
345                 350                 355                 360

GAT GAG CTT TAT TTC TTG TTC GAG CTG TTC AGC GAC CAT TTT CAC GTT         1276
Asp Glu Leu Tyr Phe Leu Phe Glu Leu Phe Ser Asp His Phe His Val
                365                 370                 375

TCA TCC AAA AGT TCA TTA CAT ATG AAC TTC ATG TCC TCA CAC TCA AAC         1324
Ser Ser Lys Ser Ser Leu His Met Asn Phe Met Ser Ser His Ser Asn
            380                 385                 390
```

-continued

```
AAC ATC CAC GCC CTC GAG CAA CTA AGG TGT ACA AAG AAC AAA GCA ACC     1372
Asn Ile His Ala Leu Glu Gln Leu Arg Cys Thr Lys Asn Lys Ala Thr
        395                 400                 405

AAT TTC TCT CAA TTT GTT AAG AAA ATG ATG GCT TCC TTG CCT TGT AGT     1420
Asn Phe Ser Gln Phe Val Lys Lys Met Met Ala Ser Leu Pro Cys Ser
    410                 415                 420

TGT CAG TCT CAG AGT CCT TCC CCA TAT TTT GAC CAA TCT CTC TTC AGG     1468
Cys Gln Ser Gln Ser Pro Ser Pro Tyr Phe Asp Gln Ser Leu Phe Arg
425                 430                 435                 440

TTT GAC GAG AAG CTT ATT TCA GCT ATT GAC CGC CAT AGA CAG TCT ACT     1516
Phe Asp Glu Lys Leu Ile Ser Ala Ile Asp Arg His Arg Gln Ser Thr
                445                 450                 455

GAC CAT CCA ATC AAA TTC ATT TCT AGA AGA CAA CCC AAT ATC CTG AAA     1564
Asp His Pro Ile Lys Phe Ile Ser Arg Arg Gln Pro Asn Ile Leu Lys
            460                 465                 470

TTC AAA ATG AAG CCA GGA CCT GAA GCT GGC AGC ACA GAT GGG CGA ACT     1612
Phe Lys Met Lys Pro Gly Pro Glu Ala Gly Ser Thr Asp Gly Arg Thr
        475                 480                 485

AAG AAG ATC TGT TCC TTC CTC TTC CAC CCA ATA TTA CCC CTT GCA CTT     1660
Lys Lys Ile Cys Ser Phe Leu Phe His Pro Ile Leu Pro Leu Ala Leu
    490                 495                 500

TCT GTT CAA CAA ACC TTG TTT CTG CAG GCA TCA GTT GTA AAT ATC CAT     1708
Ser Val Gln Gln Thr Leu Phe Leu Gln Ala Ser Val Val Asn Ile His
505                 510                 515                 520

TTT CGT CGA TAA TGTAAAAACT TAATTTATAT GTTACCGATT TGTTTATAAA         1760
Phe Arg Arg *

TTTCTCTAAT AACCTCTAGA TTGAAATCAA CCTAGAAATC ACAAATTCAT CATAACAGAG   1820

CCGTAGATGC TAGTGTCTTT GACTTCTACA TTTTCTTTGT TACAAGAATC AAACAAATGC   1880

TTGATAGAGT GCCAAGACGG TTAGTATGGG TATAAGGATT AGTTCTTCTG TAAGTTTTTG   1940

TTACAGCTTC TCTTCTAATT AATTGATGTA CATTCAGATG TTAAAAAAAA AAAAAAAAAA   2000
```

(2) INFORMATION FOR SEQ ID NO: 2:

(i) SEQUENCE CHARACTERISTICS:
        (A) LENGTH: 523 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Phe Lys Thr Asn Asn Val Thr Ala Arg Leu Phe Glu Arg Gln Ile
1               5                   10                  15

Cys Thr Pro Ala Pro Gly Thr Ser Ile His Arg Ala Arg Arg Phe Tyr
            20                  25                  30

Glu Asn Val Val Pro Ser Tyr Thr Ile Tyr Asp Val Glu Cys Pro Asp
        35                  40                  45

His Ser Phe Arg Lys Phe Thr Asp Asp Gly Leu Tyr Phe Val Ser Phe
    50                  55                  60

Ser Arg Asn His Gln Asp Leu Val Val Tyr Arg Pro Thr Trp Leu Thr
65                  70                  75                  80

Phe Ser Cys Lys Glu Glu Asp Cys Asp Thr His Asp Leu Pro Leu Lys
                85                  90                  95

Ala Arg Lys Phe Glu Ser Phe Thr Gln Leu Tyr Ser Val Thr Leu
            100                 105                 110

Ala Ser Ser Gly Glu Leu Ile Cys Lys Asp Phe Phe Leu Tyr Met Glu
        115                 120                 125
```

```
Ser Asn Gln Phe Gly Leu Phe Ala Thr Ser Thr Ala Gln Ile His Asp
    130                 135                 140

Ala Pro Pro Thr Gly Gly Ala Ile Gln Gly Val Pro Ser Val Glu Lys
145                 150                 155                 160

Ile Thr Phe His Leu Leu Arg Leu Val Asp Gly Ala Ile Leu Asp Glu
                165                 170                 175

Arg Val Phe His Asn Asp Tyr Val Asn Leu Ala His Ser Ile Gly Ala
            180                 185                 190

Phe Leu Tyr Asp Asp Leu Leu Ala Ile Val Ser Leu Arg Tyr Gln Arg
        195                 200                 205

Ile His Ile Leu Gln Ile Arg Asp Ser Gly Asp Leu Val Asp Val Arg
    210                 215                 220

Ala Ile Gly Glu Phe Cys Arg Glu Asp Asp Glu Leu Phe Leu Asn Ser
225                 230                 235                 240

Asn Ser Gln Val Leu Val Asn His Val Gly Asn Gly Phe His His Ser
                245                 250                 255

Leu Pro Gln Ser Glu Thr Ser Phe Leu Ser Gly Ile Lys Gln Arg Leu
            260                 265                 270

Leu Ser Tyr Ile Phe Arg Gly Ile Trp Asn Glu Ala Asp Gln Thr Met
        275                 280                 285

Arg Val Gln Cys Leu Lys Lys Lys Phe Tyr Phe His Phe Gln Asp Tyr
    290                 295                 300

Ile Asp Leu Ile Ile Trp Lys Val Gln Phe Leu Asp Arg His His Leu
305                 310                 315                 320

Leu Ile Lys Phe Gly Ser Val Asp Gly Gly Val Ser Arg Asn Ala Asp
                325                 330                 335

Ile His Pro Ser Phe Phe Ala Val Tyr Asn Met Glu Thr Thr Glu Ile
            340                 345                 350

Val Ala Phe Tyr Gln Asn Ser Ala Asp Glu Leu Tyr Phe Leu Phe Glu
        355                 360                 365

Leu Phe Ser Asp His Phe His Val Ser Ser Lys Ser Ser Leu His Met
    370                 375                 380

Asn Phe Met Ser Ser His Ser Asn Asn Ile His Ala Leu Glu Gln Leu
385                 390                 395                 400

Arg Cys Thr Lys Asn Lys Ala Thr Asn Phe Ser Gln Phe Val Lys Lys
                405                 410                 415

Met Met Ala Ser Leu Pro Cys Ser Cys Gln Ser Gln Ser Pro Ser Pro
            420                 425                 430

Tyr Phe Asp Gln Ser Leu Phe Arg Phe Asp Glu Lys Leu Ile Ser Ala
        435                 440                 445

Ile Asp Arg His Arg Gln Ser Thr Asp His Pro Ile Lys Phe Ile Ser
    450                 455                 460

Arg Arg Gln Pro Asn Ile Leu Lys Phe Lys Met Lys Pro Gly Pro Glu
465                 470                 475                 480

Ala Gly Ser Thr Asp Gly Arg Thr Lys Lys Ile Cys Ser Phe Leu Phe
                485                 490                 495

His Pro Ile Leu Pro Leu Ala Leu Ser Val Gln Gln Thr Leu Phe Leu
            500                 505                 510

Gln Ala Ser Val Val Asn Ile His Phe Arg Arg
        515                 520
```

(2) INFORMATION FOR SEQ ID NO: 3:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 3:

CATCAACACT GCCAAAC                                                    17

(2) INFORMATION FOR SEQ ID NO: 4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 4:

GAAAGCAGCC GTTGCT                                                     16

(2) INFORMATION FOR SEQ ID NO: 5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 5:

AGTTCATCAT CTTCACGGC                                                  19

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 6:

GTATGATTCA CTAGTTTAAT GCTGCTGAAA G                                    31

(2) INFORMATION FOR SEQ ID NO: 7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 7:

CCCATACTAG TCGTCTTGGC ACTCTATCAA G                                    31

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 8:

GAAGGTAATT TTATATTAAA CATAGA                                          26

(2) INFORMATION FOR SEQ ID NO: 9:

(i) SEQUENCE CHARACTERISTICS:
        (A) LENGTH: 28 base pairs

-continued

```
        (B) TYPE: nucleic acid
        (C) STRANDEDNESS: single
        (D) TOPOLOGY: linear (xi) SEQUENCE DESCRIPTION: SEQ ID NO: 9:

GTGATTTCTA GGTTGATTTG AATCTAGA                                          28

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 10:

CAAATCGGTA ACATAT                                                       16

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 11:

GGGGAAGCTT TTTCACGAAA TCGGCCCTTA                                        30

(2) INFORMATION FOR SEQ ID NO: 12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 12:

CCCGGATCCT TCTTTTGCAC TGTGAATGAT TAG                                    33
```